(12) United States Patent
Zuo

(10) Patent No.: US 6,800,303 B2
(45) Date of Patent: Oct. 5, 2004

(54) PROCESS OF MAKING A SUPPLEMENT FOR DIGESTIVE AILMENT

(76) Inventor: Xiao-Feng Zuo, Room 602, No. 26, Lane 300, Langao Rode, Shanghai (CN), 200061

( * ) Notice: Subject to any disclaimer, the term of this patent is extended or adjusted under 35 U.S.C. 154(b) by 0 days.

(21) Appl. No.: 10/195,161

(22) Filed: Jul. 16, 2002

(65) Prior Publication Data

US 2004/0013745 A1 Jan. 22, 2004

(51) Int. Cl.⁷ ............................................. A61K 35/78
(52) U.S. Cl. ...................... 424/725; 424/757; 424/773; 424/776; 424/777; 426/648
(58) Field of Search .............................. 424/725, 757, 424/773, 776, 777; 426/648

(56) References Cited

U.S. PATENT DOCUMENTS 4,987,150 A * 1/1991 Kurono et al.

FOREIGN PATENT DOCUMENTS

| CN | 1080868 | * | 1/1994 |
| CN | 1126086 | * | 7/1996 |
| CN | 1220163 | * | 6/1999 |
| CN | 1234243 | * | 11/1999 |

* cited by examiner

Primary Examiner—Christopher R. Tate
(74) Attorney, Agent, or Firm—Raymond Y. Chan; David and Raymond Patent Group

(57) ABSTRACT

A process of making a supplement for digestive ailment includes the steps of (a) soaking a raw composition which consists of 39.22% by weight of Radix Angelicae Sinensis, 39.22% by weight of Radix Paeoniae Alba, 3.92% by weight of Semen Arecae, 5.88% by weight of Talcum, 1.96% by weight of Radix Saussureae Lappae, 1.96% by weight of Semen Raphani, 3.92% by weight of Fructus Aurantii, and 3.92% by weight of Radix Glycyrrhizae, in a predetermined volume of water for a predetermined soaking time to form a pre-decocting solution and a pre-decocting composition; (b) heating said pre-decocting solution and said pre-decocting composition for a predetermined period of decocting time to form a mixture consisting of a residual composition and a supplement in solution; wherein a volume ratio of said supplement in solution and said water in the step (a) is approximately 1:3; and (c) separating said residual composition and said supplement in solution.

24 Claims, 5 Drawing Sheets

Heating the residual composition in a predetermined amount of second serving water to form a second mixture which consists of a second residual composition and a second supplement solution Separating the second residual composition and the second supplement in solution

| Chinese Pinyin | Name in Latin | Name of herbs in Chinese Character |
|---|---|---|
| Dang Gui | *Radix Angelicae Sinensis* | 當歸 |
| Bai Shao | *Radix Paeoniae Alba* | 白芍 |
| Bing Lang | *Semen Arecae* | 檳榔 |
| Hua Shi | *Talcum* | 滑石 |
| Hua Shi Mo | *Pulvis Talci* | 滑石末 |
| Guang Mu Xiang | *Radix Saussureae Lappae* | 廣木香 |
| Luo Bo Zi | *Semen Raphani* | 蘿卜子 |
| Zhi Ke | *Fructus Aurantii* | 枳殼 |
| Gan Cao | *Radix Glycyrrhizae* | 甘草 |

FIGURE 5

PROCESS OF MAKING A SUPPLEMENT FOR DIGESTIVE AILMENT

BACKGROUND OF THE PRESENT INVENTION

1. Field of Invention

The present invention relates to a process of making a supplement for digestive ailment, and more particularly to making a supplement for digestive ailment for promoting the health of digestive system of human bodies.

2. Description of Related Arts

Health is a kind of balance of our bodies and the environment. Any forms of imbalance in our bodies will initiate the generation of signals from our bodies. Proper reaction should be done for the signal to restore our bodies to normal. If we neglect the signals from our bodies, we will gradually feel uncomfortable and eventually get sick.

The importance of the balance of our bodies can be easily shown in our daily lives. For example, when our bodies suffer from deficiency of water, we will feel thirsty. The sense of feeling thirsty is a signal from our bodies to alert us the necessity of drinking water for our bodies. Therefore, when we receive the signal of feeling thirsty, we may act by drinking water to restore our bodies to normal. However, if we ignore the signal, the level of deficiency of water will gradually increase and our bodies will become very uncomfortable. Under prolonged situation of suffering water deficiency, we will start to get sick and will eventually die of dehydration.

We can always take remedial steps by ourselves to restore the balance of our bodies. For example, if we have insufficient sleep, we will feel tired. We have the signal of feeling tired and our bodies will act by slowing down the metabolic activities of our bodies. Therefore, we consume less energy in our daily work and decrease the seriousness of our tiredness. Though we still need to have a rest to restore the balance of our bodies, the act of slowing down metabolic activities of our bodies is an automatic remedial step by ourselves that helps to maintain the balance of our bodies.

However, sometimes our bodies cannot withstand the imbalance and our automatic remedial step by ourselves is not fast and sensitive enough in responsive to our imbalance. Therefore, some external precautious steps are required to speed up our remedial action from our bodies and maintain the balance of our bodies.

One of the common signals arisen from the imbalance of our bodies is gastrointestinal pain and discomfort. The pain is a signal from our bodies to alert us to pay attention to our diet and take a rest. However, it is always unrealistic to take a rest for this kind of gastrointestinal pain and discomfort. Therefore, instead of ignoring the signal from our bodies that may lead to serious adverse consequence, it is better for us to take some extra care to our bodies for restoring the balance.

Common method of curing this kind of pain is taking medicine, such as anodyne and aspirin, for soothing the pain. However, this can only help to soothing the pain, but is useless in restoring the balance of our bodies.

Herbs have been widely used to restore any imbalance of our bodies, especially when we encounter the gastrointestinal pain and discomfort, and the effect of the use of herbs has been highly recognized. Although many different kinds of herbs can be used independently for achieving their functions. However, the use of single herb is not competent to maintain the balance of our bodies. Therefore, there are always difficulties in making and preparing a suitable composition for our use.

SUMMARY OF THE PRESENT INVENTION

The main object of the present invention is to provide a process of making a supplement for digestive ailment which is a composition of natural herbs for promoting the process of natural restoring activities of digestive system of human bodies.

Another object of the present invention is to provide a process of making a supplement for digestive ailment which is a composition of natural herbs for increasing blood flow to digestive system of human bodies.

Another object of the present invention is to provide a process of making a supplement for digestive ailment which is a composition of natural herbs for decreasing pressure transiently and releasing gastrointestinal pain or discomfort of human bodies.

In order to accomplish the above objects, the present invention provides a process of making a supplement for digestive ailment which is a composition of natural herbs, wherein the supplement for digestive ailment having a preferred composition which consists of 39.22% by weight of Radix Angelicae Sinensis, 39.22% by weight of Radix Paeoniae Alba, 3.92% by weight of Semen Arecae, 5.88% by weight of Talcum, 1.96% by weight of Radix Saussureae Lappae, 1.96% by weight of Semen Raphani, 3.92% by weight of Fructus Aurantii, and 3.92% by weight of Radix Glycyrrhizae.

The process of making a supplement for digestive ailment comprises the steps of:

1a. soaking a raw composition which consists of Radix Angelicae Sinensis, Radix Paeoniae Alba, Semen Arecae, Talcum, Radix Saussureae Lappae, Semen Raphani, Fructus Aurantii, and Radix Glycyrrhizae, in a predetermined amount of water for a predetermined of time to form a pre-decocting solution and a pre-decocting composition;

1b. heating the pre-decocting solution and the pre-decocting composition for a predetermined period of time to form a mixture consisting of a residual composition and a supplement in solution; wherein a volume ratio of the supplement in solution and the water in step 1 is approximately 1:3; and 1c. separating the residual composition and the supplement in solution.

The residual composition may be used to prepare a second supplement for digestive ailment which comprises the steps of:

2a. heating the residual composition in a predetermined amount of water for a predetermined amount of time to form a mixture which consists of a second residual composition and a second supplement solution; and 2b. separating the second residual composition to make a second supplement solution.

BRIEF DESCRIPTION OF THE DRAWINGS

FIG. 5 is a table of original Chinese names and Chinese pinyin of the herbs used in the composition of the supplement for digestive ailment of the present invention.

DETAILED DESCRIPTION OF THE PREFERRED EMBODIMENT

Figure 1:
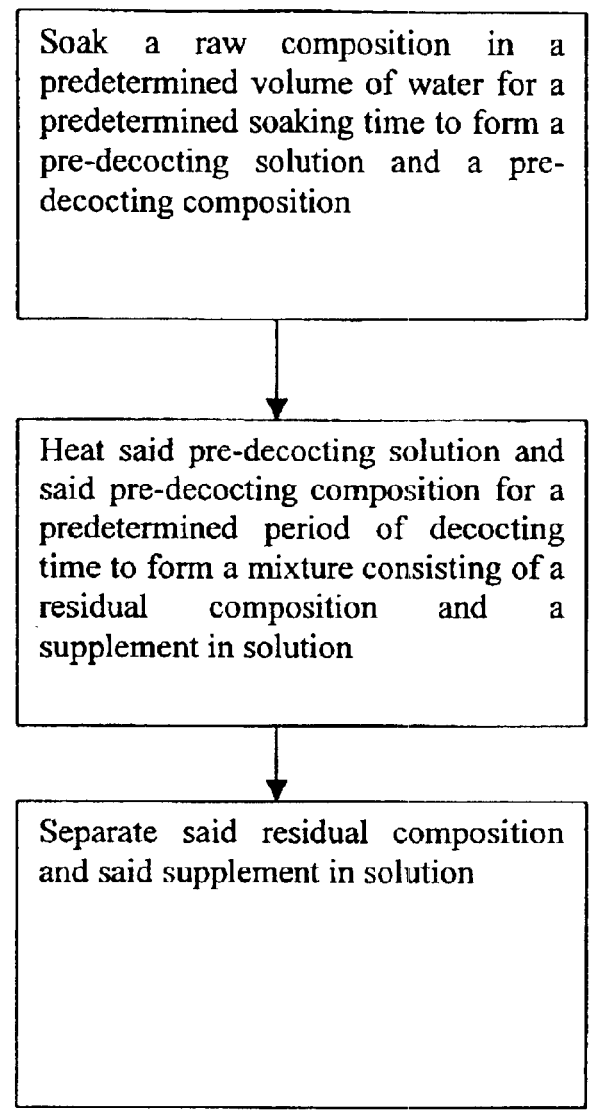
FIG. 1 is a box diagram of a principal process of making a supplement for digestive ailment

Referring to FIG. 1, the present invention provides a principal process of making a supplement for digestive ailment which is a composition of natural herbs, wherein the supplement for digestive ailment has a preferred composition which consists of 39.22% by weight of Radix Angelicae Sinensis, 39.22% by weight of Radix Paeoniae Alba, 3.92% by weight of Semen Arecae, 5.88% by weight of Talcum, 1.96% by weight of Radix Saussureae Lappae, 1.96% by weight of Semen Raphani, 3.92% by weight of Fructus Aurantii, and 3.92% by weight of Radix Glycyrrhizae.

Radix Angelicae Sinensis Radix Angelicae Sinensis has been used as Chinese herbal medicine and dietary supplement. Medical research has revealed its medical significance and common prescription as dietary supplement has validated its beneficiary effects to human bodies. Radix Angelicae Sinensis has been used to enrich blood, promote blood circulation and moisturize dryness, and loose bowel by dilating coronary artery, increasing coronary flow and decreasing oxygen consumption, lowering the level of blood lipids and countering the development of atheroma with its action components ferulic acid, promoting the phagocytosis of mononuclear macrophage, and protecting the liver from damage and increasing biliary secretion. Thus, it is widely used for increasing the blood circulation and increasing the rate of metabolism.

Radix Paeoniae Alba has been used for soothing the liver and alleviating pain by lowering blood pressure transiently and inhibiting the central nervous system.

Semen Arecae has the effect of accelerating the secretion of digestive juices and promoting appetite for activating circulation of vital energy and relieving dyspepsia. Overdose may cause salivation, vomiting, lethargy and convulsion.

Talcum has been used for clearing away heat, promoting diuresis and relieving stranguria, depriving dampness to stop diarrhea. Pulvis Talci is a treated powdered form of Talcum.

Radix Saussureae Lappae has been used for promoting circulation of the body.

Semen Raphani has been used for promoting digestion and relieving dyspepsia, and lowering blood pressure by its active component, Raphanin, that inhibits growth of Staphylococcus and Bacillus in vitro and its anti-inflammatory effect.

Fructus Aurantii has been used for regulating the circulation of the body, removing stagnation, and alleviating distension.

Radix Glycyrrhizae has chief active components glycyrrhizin, glycyrrhetinic acid, ligquiritin and liquiritigenin and its extract and glycyrrhizin exerts a detoxifying effect and anti-inflammatory effect. However, overdose may lead to edema and hypertension.

The present invention provides a principal process of making a supplement for digestive ailment, which comprises the steps of:

1a. soaking a raw composition which includes Radix Angelicae Sinensis, Radix Paeoniae Alba, Semen Arecae, Talcum, Radix Saussureae Lappae, Semen Raphani, Fructus Aurantii, and Radix Glycyrrhizae, in a predetermined volume of water for a predetermined of soaking time to form a pre-decocting solution and a pre-decocting composition;

1b. heating the pre-decocting solution and the pre-decocting composition for a predetermined period of time to form a mixture including a residual composition and a supplement in solution; wherein a volume ratio of the supplement in solution and the water in step 1a is approximately 1:3; and 1c. separating the residual composition and the supplement in solution.

The ratio of the weight of the raw composition and the volume of water is approximately 3:10. For example, one serving of the supplement for digestive ailment may be prepared by using 60 grams of Radix Angelicae Sinensis, 60 grams of Radix Paeoniae Alba, 6 grams of Semen Arecae, 9 grams of Talcum, 3 grams of Radix Saussureae Lappae, 3 grams of Semen Raphani, 3 grams of Fructus Aurantii, and 6 grams of Radix Glycyrrhizae in 500 ml of water.

When the raw composition of the supplement for digestive ailment is soaked in the predetermined volume of water, the water will be able to penetrate into the raw composition by osmosis and diffusion and soften the raw composition. The preferred soaking time is 30 minutes.

After the predetermined period of soaking time, the pre-decocting solution and the pre-decocting composition will be saturated. Then, heating the pre-decocting composition and the pre-decocting solution will increase the temperature and maintain an optimum environment for reaction activity of the pre-decocting composition and the pre-decocting solution and will shorten the time to reach a equilibrium to form a saturated solution of the supplement.

Then, the reaction activity is completed and a predetermined volume of supplement in solution is obtained. Thus, the supplement in solution is separated from the residual composition for oral administration.

The residual composition and the supplement in solution can be separated by filtration.

Figure 2:
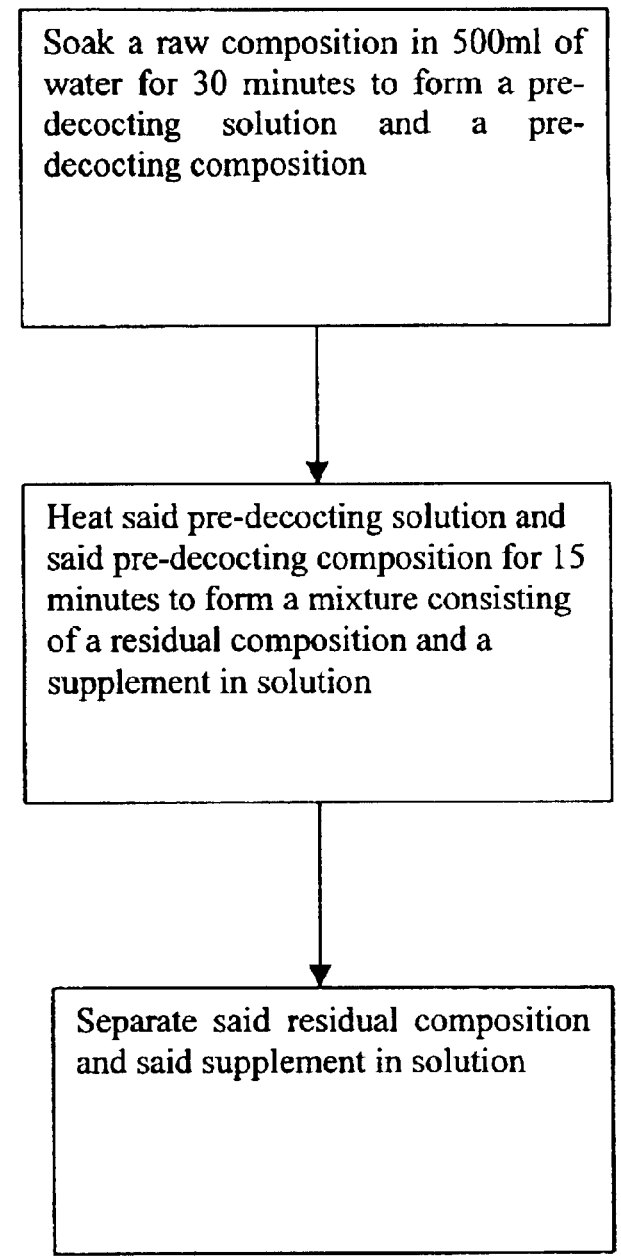
FIG. 2 is a box diagram of a principal process of making a supplement for digestive ailment for one serving.

Referring to FIG. 2, the present invention provides a principal process of making a supplement for digestive ailment for one serving, wherein the raw composition of a supplement consists of 60 grams of Radix Angelicae Sinensis, 60 grams of Radix Paeoniae Alba, 6 grams of Semen Arecae, 9 grams of Talcum, 3 grams of Radix Saussureae Lappae, 3 grams of Semen Raphani, 3 grams of Fructus Aurantii, and 6 grams of Radix Glycyrrhizae, wherein 500 ml of water is used for soaking the raw composition.

The soaking time is approximately 30 minutes and the decocting time is approximately 15 minutes, wherein the heating process boils and evaporates the pre-decocting solution such that the volume of supplement in solution is one-third of the volume of the water.

Figure 3:
FIG. 3 is a box diagram of a supplementary process of making a supplement for digestive ailment.

Referring to FIG. 3, the present invention provides a supplementary process for making a supplement for digestive ailment, wherein the residual composition obtained from the principal process may be used to prepare a supplement for digestive ailment which comprises the steps of:

a. heating the residual composition from the principal process in a predetermined amount of second serving water to form a second mixture which consists of a second residual composition and a second supplement solution, wherein a volume ratio of the second supplement in solution and the second serving water in step 2a is approximately 1:3; and b. separating the second residual composition and the second supplement in solution.

Figure 4:
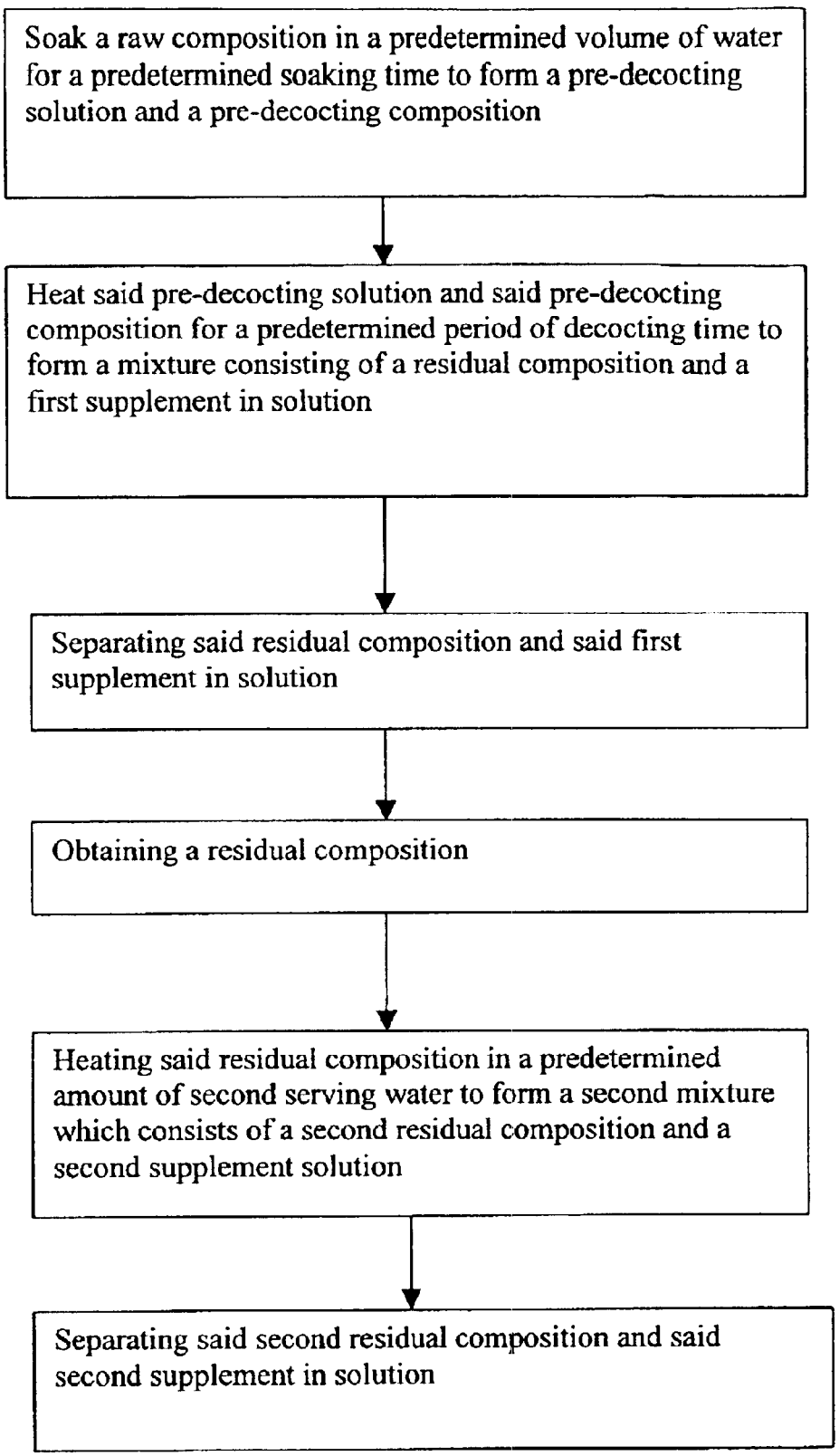
FIG. 4 is a box diagram of a combined process of making a supplement for digestive ailment.

Referring to FIG. 4, the present invention provides a combined process of making a supplement for digestive ailment comprising the steps of:

a. soaking a raw composition which consists of 39.22% by weight of Radix Angelicae Sinensis, 39.22% by weight of Radix Paeoniae Alba, 3.92% by weight of Semen Arecae, 5.88% by weight of Talcum, 1.96% by weight of Radix Saussureae Lappae, 1.96% by weight of Semen Raphani, 3.92% by weight of Fructus Aurantii, and 3.92% by weight of Radix Glycyrrhizae, in a predetermined volume of water for a predetermined soaking time to form a pre-decocting solution and a pre-decocting composition;

b. heating said pre-decocting solution and said pre-decocting composition for a predetermined period of decocting time to form a mixture consisting of a residual composition and a first supplement in solution; wherein a volume ratio of said first supplement in solution and said water in step a is approximately 1:3;

c. separating said residual composition and said first supplement in solution;

d. obtaining a residual composition;

e. heating said residual composition in a predetermined amount of second serving water to form a second mixture which consists of a second residual composition and a second supplement solution, wherein a volume ratio of said second supplement in solution and said second serving water in step e is approximately 1:3; and f. separating said second residual composition and said second supplement in solution.

The separating steps c and f can be a filtration process.

Referring to FIG. 5, the present invention is originated from the use of herbs and the name of the herbs used in the composition for digestive ailment is a translation of their Chinese names. The translation is as follows:

| Chinese Pinyin | Name in Latin | Name in Chinese Character |
| --- | --- | --- |
| Dang Gui | Radix Angelicae Sinensis | 當歸 |
| Bai Shao | Radix Paeoniae Alba | 白芍 |
| Bing Lang | Semen Arecae | 檳榔 |
| Hua Shi | Talcum | 滑石 |
| Hua Shi Mo | Pulvis Talci | 滑石末 |
| Guang Mu Xiang | Radix Saussureae Lappae | 廣木香 |
| Luo Bo Zi | Semen Raphani | 蘿卜子 |
| Zhi Ke | Fructus Aurantii | 枳殼 |
| Gan Cao | Radix Glycyrrhizae | 甘草 |

What is claimed is:

1. A process of making a supplement, comprising the steps of:

(a) soaking a raw composition which includes a 39.22% by weight of Radix Angelicae Sinensis, 39.22% by weight of Radix Paeoniae Alba, a 3.92% by weight of Semen Arecae, 5.88% by weight of Talcum, 1.96% by weight of Radix Saussureae Lappae, a 1.96% by weight of Semen Raphani, 3.92% by weight of Fructus Aurantii, and a 3.92% by weight of Radix Glycyrrhizae, wherein said raw composition is mixed in a predetermined volume of water for a predetermined soaking time to form pre-decocting composition;

(b) heating said pre-decocting composition for a predetermined period of decocting time to form a mixture consisting of a residual composition and a supplement in solution; wherein a volume ratio of said supplement in solution and said water in the step (a) is approximately 1:3; and (c) separating said residual composition and said supplement in solution.

2. The process, as recited in claim 1, wherein said soaking time is at least 30 minutes.

3. The process, as recited in claim 1, wherein in the step (c), said residual composition and said supplement in solution are separated by filtration.

4. The process, as recited in claim 2, wherein in the step (c), said residual composition and said supplement in solution are separated by filtration.

5. The process, as recited in claim 1, wherein when a serving is prepared, said raw composition includes 60 grams of said Radix Angelicae Sinensis, 60 grams of said Radix Paeoniae Alba, 6 grams of said Semen Arecae, 9 grams of said Talcum, 3 grams of said Radix Saussureae Lappae, 3 grams of said Semen Raphani, 3 grams of said Fructus Aurantii, and 6 grams of said Radix Glycyrrhizae, and said water is 500 ml in volume.

6. The process, as recited in claim 4, wherein when a serving is prepared, said raw composition includes 60 grams of said Radix Angelicae Sinensis, 60 grams of said Radix Paeoniae Alba, 6 grams of said Semen Arecae, 9 grams of said Talcum, 3 grams of said Radix Saussureae Lappae, 3 grams of said Semen Raphani, 3 grams of said Fructus Aurantii, and 6 grams of said Radix Glycyrrhizae, and said water is 500 ml in volume.

7. The process, as recited in claim 6, wherein when preparing said serving, said decocting time is 15 minutes.

8. The process, as recited in claim 1, further comprising the steps of:

(d) heating said residual composition in a predetermined amount of second serving water to form a second mixture which consists of a second residual composition and a second supplement in solution, wherein a volume ratio of said second supplement in solution and said second serving water is approximately 1:3; and (e) separating said second residual composition and said second supplement in solution.

9. The process, as recited in claim 7, further comprising the steps of:

(d) heating said residual composition in a predetermined amount of second serving water to form a second mixture which consists of a second residual composition and a second supplement in solution, wherein a volume ratio of said second supplement in solution and said second serving water is 1:3; and (e) separating said second residual composition and said second supplement in solution.

10. The process, as recited in claim 8, wherein in the step (e), said second residual composition and said second supplement in solution are separated by filtration.

11. The process, as recited in claim 9, wherein in the step (e), said second residual composition and said second supplement in solution are separated by filtration.

12. The supplement, as recited in claim 1, wherein said Talcum is powdered Talcum.

13. The supplement, as recited in claim 5, wherein said Talcum is powdered Talcum.

14. A supplement produced by a process which comprises the steps of:

(a) soaking a raw composition which includes a 39.22% by weight of Radix Angelicae Sinensis, 39.22% by weight of Radix Paeoniae Alba, 3.92% by weight of Semen Arecae, 5.88% by weight of Talcum, 1.96% by weight of Radix Saussureae Lappae, 1.96% by weight of Semen Raphani, a 3.92% by weight of Fructus Aurantii, and 3.92% by weight of Radix Glycyrrhizae, wherein said raw composition is mixed in a predetermined volume of water for a predetermined soaking time to form a pre-decocting solution and a pre-decocting composition;

(b) heating said pre-decocting solution and said pre-decocting composition for a predetermined period of decocting time to form a mixture consisting of a residual composition and a supplement in solution; wherein a volume ratio of said supplement in solution and said water in the step (a) is 1:3; and (c) separating said residual composition and said supplement in solution.

15. The process, as recited in claim 14, wherein in the step (c), said residual composition and said supplement in solution are separated by filtration.

16. The supplement, as recited in claim 15, wherein said soaking time is at least 30 minutes.

17. The supplement, as recited in claim 16, wherein when a serving is prepared, said raw composition includes 60 grams of said Radix Angelicae Sinensis, 60 grams of said Radix Paeoniae Alba, 6 grams of said Semen Arecae, 9 grams of said Talcum, 3 grams of said Radix Saussureae Lappae, 3 grams of said Semen Raphani, 3 grams of said Fructus Aurantii, and 6 grams of said Radix Glycyrrhizae, and said water is 500 ml in volume.

18. The supplement, as recited in claim 17, wherein when preparing said serving, said decocting time is 15 minutes.

19. The supplement, as recited in claim 14, wherein the process further comprises the steps of:

(d) heating said residual composition in a predetermined amount of second serving water to form a second mixture which consists of a second residual composition and a second supplement in solution, wherein a volume ratio of said second supplement in solution and said second serving water is 1:3; and (e) separating said second residual composition and said second supplement in solution.

20. The supplement, as recited in claim 18, wherein the process further comprises the steps of:

(d) heating said residual composition in a predetermined amount of second serving water to form a second mixture which consists of a second residual composition and a second supplement in solution, wherein a volume ratio of said second supplement in solution and said second serving water is approximately 1:3; and (e) separating said second residual composition and said second supplement in solution.

21. The supplement, as recited in claim 19, wherein in the step (e), said second residual composition and said second supplement in solution are separated by filtration.

22. The supplement, as recited in claim 20, wherein in the step (e), said second residual composition and said second supplement in solution are separated by filtration.

23. The supplement, as recited in claim 14, wherein said Talcum is powdered Talcum.

24. The supplement, as recited in claim 17, wherein said Talcum is powdered Talcum.

* * * * *